United States Patent
Fredericks

(10) Patent No.: US 6,691,047 B1
(45) Date of Patent: Feb. 10, 2004

(54) CALIBRATION OF PUMPS, SUCH AS BLOOD PUMPS OF DIALYSIS MACHINE

(75) Inventor: Chris N. Fredericks, Lake Bluff, IL (US)

(73) Assignee: Aksys, Ltd., Lincolnshire, IL (US)

(*) Notice: Subject to any disclaimer, the term of this patent is extended or adjusted under 35 U.S.C. 154(b) by 0 days.

(21) Appl. No.: 09/527,327

(22) Filed: Mar. 16, 2000

(51) Int. Cl.7 .................................................. G01F 7/00
(52) U.S. Cl. ............................ 702/47; 702/19; 702/31; 702/50; 702/98; 604/4.01; 604/67; 604/118; 604/246; 422/33; 422/81; 422/208; 128/867; 128/204.18
(58) Field of Search .............................. 702/19, 21, 31, 702/32, 45, 47, 50, 55, 85, 100, 98, 104, 105, 114, 138–140, 182, 183, 188, FOR 115, 119, 134, 135, 143, 156, 163, 170, 171; 604/4.01, 6.11, 6.61, 29, 30, 67, 118, 246, 247, 151, 31; 73/168; 417/63, 22, 18; 422/33, 81, 82, 13, 112, 113, 118, 208, 226; 128/867, 203.14, 204.18, 900, DIG. 12

(56) References Cited

U.S. PATENT DOCUMENTS

| | | |
|---|---|---|
| 4,322,972 A | 4/1982 | Karjala |
| 4,432,230 A | 2/1984 | Stahler et al. |
| 4,715,786 A | 12/1987 | Wolff et al. |
| 4,769,001 A | 9/1988 | Prince |
| 4,781,525 A | 11/1988 | Hubbard et al. |
| 5,326,476 A | 7/1994 | Grogan et al. ............... 210/646 |
| 5,536,237 A | 7/1996 | Prince et al. |
| 5,591,344 A | 1/1997 | Kenley et al. |
| 5,725,776 A * | 3/1998 | Kenley et al. ............... 210/646 |
| 5,733,257 A | 3/1998 | Sternby |
| 5,744,027 A * | 4/1998 | Connell et al. ............. 210/96.2 |
| 5,932,103 A * | 8/1999 | Kenley et al. ............... 210/646 |
| 6,027,445 A * | 2/2000 | Von Bahr .................... 600/309 |
| 2001/0034422 A1 * | 10/2001 | Hartely et al. ................. 526/88 |

FOREIGN PATENT DOCUMENTS

| | | |
|---|---|---|
| DK | 744853 | 3/1975 |
| JP | 1280698 | 11/1989 |
| JP | 1303157 | 12/1989 |
| JP | 3051053 | 3/1991 |
| WO | WO9625214 | 8/1996 |

OTHER PUBLICATIONS

McCain Jr., et al., Correlation of Bubblepoint Pressures for Reservoir Oils, 1998, vol. 51086, pp. 1–9.*

* cited by examiner

Primary Examiner—Marc S. Hoff
Assistant Examiner—Elias Desta
(74) Attorney, Agent, or Firm—McDonnell Boehnen Hulbert & Berghoff

(57) ABSTRACT

A method of calibrating a pump that is subject to variations in flow rate based on inlet pressure variations, such as a peristaltic pump found in medical instruments. The pressure at the inlet of the pump is measured and recorded during prior uses of the pump. A mean or average inlet pressure is derived from the measurements, either directly or indirectly from the measurements of using regression techniques, as a way of forecasting the inlet pressure during the next use of the pump. The pump is then calibrated at an inlet pressure that is set or adjusted to match the mean or average inlet pressure. The calibration is thus accurately performed for the pump, and is independent of the absolute accuracy of the inlet pressure sensor.

20 Claims, 3 Drawing Sheets

CALIBRATION OF PUMPS, SUCH AS BLOOD PUMPS OF DIALYSIS MACHINE

BACKGROUND OF THE INVENTION

A. Field of the Invention

This invention relates to the subject of calibration of pumps, and in particular to calibration of pumps in which the inlet pressure of the pump effects the volume of fluid moved per revolution of pump. The method involves recording the inlet pressure during use of the pump and using the recorded pressures to calibrate the pump prior to the next operation of the pump. The method is particularly suitable for use in calibrating a blood pump found in an extracorporeal circuit of a dialysis machine.

B. Description of Related Art

Hemodialysis machines are used for treating patients suffering from inadequate kidney function. Hemodialysis machines include, among other things, an extracorporeal blood circuit typically comprising an arterial line, a blood pump, a dialyzer and a venous line. Blood is removed from the patient via the arterial line and pumped by the blood pump to the dialyzer, where blood-borne toxins and excess fluids are removed from the patient's blood. The blood is then returned to the patient via the venous line. The blood pump in most dialysis machines is a peristaltic pump, wherein the pump segment is squeezed by a pair of rollers that move over a given length of pump segment tubing installed in the blood pump.

The quality of the dialysis treatment is directly related to the control over the amount of the patient's blood that flows through the dialyzer. Blood flow inaccuracy, often due to inaccurate blood pump calibration, is well known in dialysis clinics. These inaccuracies can be due to the fact that the inlet pressure to the blood pump (typically measured in the arterial line) has a significant effect upon the stroke volume of peristaltic pumps. In addition, where the pump segment and entire extracorporeal circuit are reused and subject to heat disinfection cycles between use, the heat can affect the pump segment itself, thereby changing the characteristics of the pump segment in the next use of the extracorporeal circuit. This phenomenon again changes the stroke volume of the blood pump and makes precise calibration more difficult.

The present invention provides a way of precisely calibrating the pump which compensates or accounts for the variations in inlet pressure to the blood pump and which can account for changes in the blood pump segment over time. Although the specific embodiment described herein is for calibrating a peristaltic blood pump, it should be appreciated that the calibration method can be applied to any type of pump where an inlet pressure versus flow rate relationship exists. Additionally, the calibration method is applicable outside the field of dialysis.

SUMMARY OF THE INVENTION

A method is provided for operating a pump that is subject to repeated uses. The invention provides for calibrating the pump at an expected inlet pressure that is derived from previous measurements of inlet pressure during a prior use of the pump. The result is a more accurate calibration of the pump. Further, the accurate calibration is performed independent of the accuracy of the device that is used to measure inlet pressure.

In a representative embodiment, the pump is placed in a fluid conduit which has a pre-pump or inlet pressure sensor. The method involves recording the inlet pressure in the fluid conduit during use of the pump. For example, in a blood pump embodiment, during dialysis treatments the inlet pressure to the blood pump is measured periodically and recorded in a computer readable memory that is part of the control system for the dialysis machine. At any time when the system slows or stops the blood pump (such as in the case of an alarm), the pressure recordings are paused.

The method continues by deriving (e.g., calculating) from the recordings of inlet pressure a mean or average inlet pressure at the pump that occurred during the use of the pump. In the dialysis embodiment, the average pressure over the course of the dialysis treatment is calculated. Furthermore, over multiple uses of the pump, such as multiple dialysis sessions, the average inlet pressure over multiple dialysis treatments can be averaged or regressed to arrive at a predicted inlet pressure for the next treatment or use of the pump, a pressure referred to herein as $P_c$ or calibration pressure.

The method continues by calibrating the flow rate of the pump, with the calibrating performed while the inlet pressure to the fluid conduit is set to the mean inlet pressure or the calibration pressure $P_c$ (either directly, or by varying the pressure in regular periodic intervals around the calibration pressure $P_c$). This "smart point" calibration is thus made at an inlet pressure that is likely to be experienced in the next use of the pump, and thus tends to produce a better and more accurate calibration since variation in pump flow rate as a function of inlet pressure is accounted for.

Calibration of the pump can by made by moving a known volume of fluid from a source of fluid, such as a reserve tank or ultrafiltration tank in a dialysis embodiment, at a predetermined pump RPM and sending the fluid to drain. Again, this step of moving the known volume of fluid is done while the inlet pressure to the pump is maintained at the expected inlet pressure for the next use of the pump. The time to move the fluid is automatically recorded. The known volume of fluid divided by the time yields the flow rate. The flow rate divided by RPM gives volume per revolution.

Typically, this calibrated value of volume per revolution is used by the control system software during the next dialysis treatment to control the amount of dialysis of the patient that takes place. Thus, the method continues by subsequently using the pump after having been calibrated as described. In a typical example, the pump is operated at a flow rate that is calibrated in accordance with the expected inlet pressure.

In another aspect of the invention, a method of calibrating a peristaltic blood pump of a hemodialysis machine is provided. The hemodialysis machine has an extracorporeal circuit comprising an arterial line, a venous line, and a dialyzer, wherein the blood pump pumps blood from a patient through the arterial line and dialyzer and delivers the blood back to the patient via the venous line. The method comprises the steps of:

recording inlet pressures in the arterial line during dialysis sessions for the patient;

deriving from the recorded inlet pressures a calibration inlet pressure $P_c$ to be used for calibration of the blood pump;

adjusting the inlet pressure of the arterial line to substantially match the calibration inlet pressure $P_c$; and moving a volume of fluid with the blood pump while maintaining the inlet pressure of the arterial line at the calibration inlet pressure $P_c$, to thereby derive a volume per revolution for the pump at the pressure $P_c$.

In a preferred embodiment, the calibration pressure calculated as described herein is verified by comparing it to the previous calibration number for the blood tubing set to see if the change is outside of a specified range. If this verification challenges the validity of the calibration, the calibration is repeated up to a predetermined number of times. If, after repeated trials, the calibration is still outside of the specified range, then the calibration is deemed to have failed. In that event, the blood tubing set is changed (i.e., replaced) and/or the blood pump is serviced.

It should be appreciated that the patient's instantaneous arterial pre-pump blood pressure may vary over the course of the treatment, and thus the flow rate of the blood pump will also vary. However, if the mean pressure is accurately predicted (as described herein) then the mean flow rate will also be set accurately and the correct dose of dialysis delivered to the patient.

In an alternative embodiment, in addition to using the "smart point" calibration of the blood pump to set the blood pump RPM during treatment, the inlet pressure measurements during the treatment may be used to actively control the RPM of the blood pump in order to achieve a constant flow rate over varying pressure.

These and other aspects of the invention will be apparent from the following description of the presently preferred embodiment of the invention.

BRIEF DESCRIPTION OF THE DRAWINGS

In the following detailed description of presently preferred and alternative embodiments of the invention, reference will be made to the accompanying drawing figures, in which like reference numerals refer to like elements in the various views, and in which.

DETAILED DESCRIPTION OF THE PREFERRED EMBODIMENT

Figure 1:
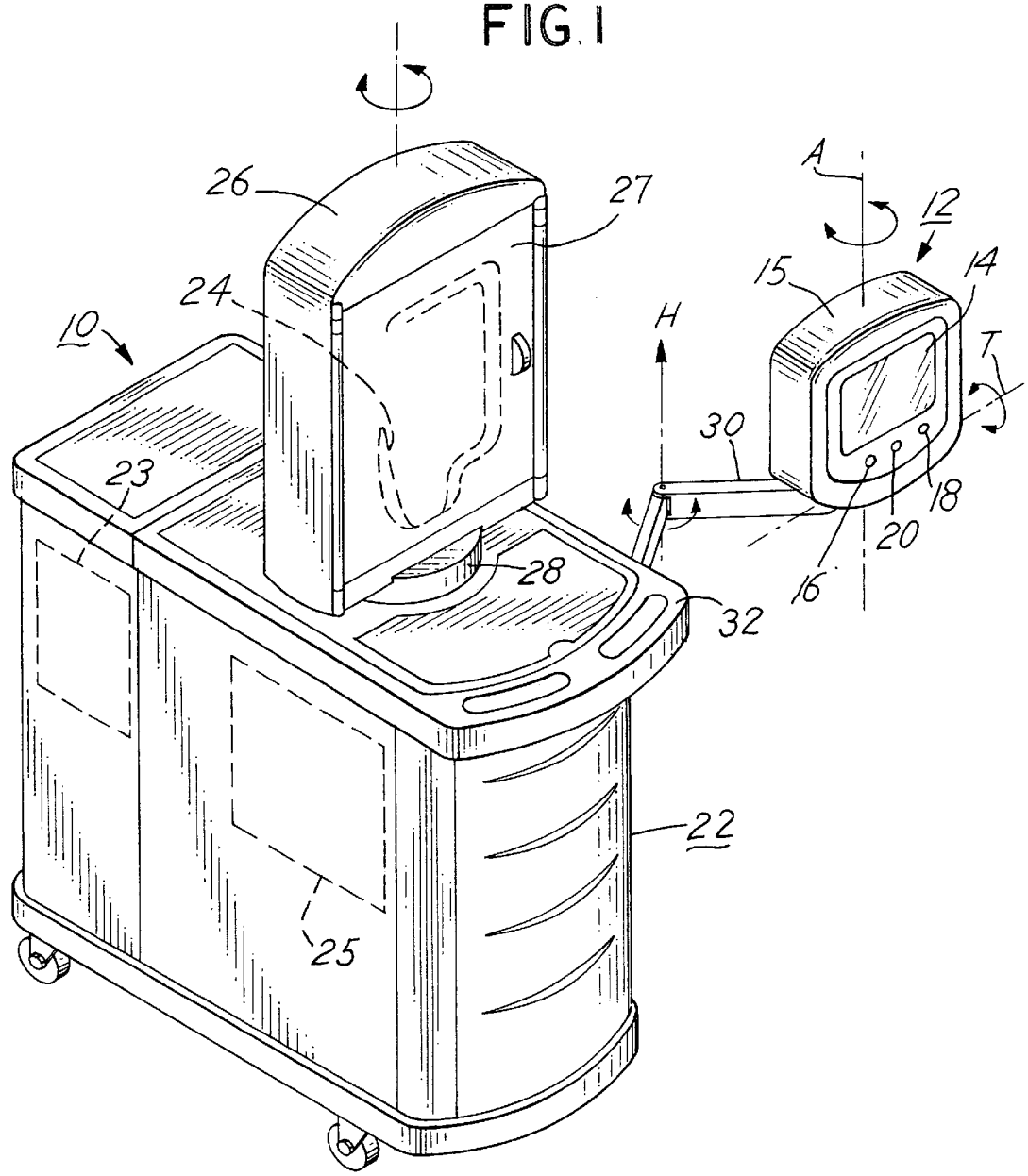
FIG. 1 is an illustration of a dialysis machine, including an extracorporeal circuit and user interface, which may be employed in practicing the invention.

FIG. 1 is an illustration of a dialysis machine 10 having a user interface 12, which may be employed in practicing the invention. The dialysis machine 10 in the illustrated embodiment is a machine suitable for use outside of a traditional dialysis clinic setting, such as the home, nursing home or self-care clinic environment, however the invention is not considered limited to such a machine. Before discussing the blood pump calibration invention in detail, a brief discussion of the dialysis machine 10 of FIG. 1 and some of the features related to the present invention will be set forth.

The dialysis machine 10 includes an extracorporeal circuit 24 mounted above a lower cabinet 22. The extracorporeal circuit is housed behind a door 27 in an enclosure 26 that is mounted to a turntable 28. The turntable 28 is moveably mounted to the top of the lower cabinet 22 such that the turntable 28, enclosure 26 and extracorporeal circuit 24 are capable of rotation as a unit relative to the lower cabinet 22 about a vertical axis.

The dialysis machine 10 has a water treatment module 23 and a dialysate preparation module 25 contained within a lower compartment or cabinet 22. The water treatment module 23 plays no part in the present invention, and is described in detail in U.S. Pat. No. 5,591,344 to Kenley et al. and assigned to Aksys, Ltd., the assignee of the present invention. The Kenley et al. U.S. Pat. No. 5,591,344 is incorporated by reference herein. Additionally, the manner in which the dialysate solutions are prepared in the dialysate preparation module 25 and circulated through a dialysate circuit to a dialyzer in the extracorporeal circuit in the enclosure 26 is not particularly important to this invention and is well known in the art, and may be as described in the Kenley et al. patent (a preferred embodiment), or otherwise.

The details as to the user interface 12 are also not particularly important insofar as the present invention is concerned, and may be as described in U.S Pat. No. 5,788,851 or as described in the above-referenced Grogan et al. patent, or otherwise. The user interface includes a touch sensitive display screen 14 and a set of three hard keys 16, 18 and 20 that are pressed by the user to enter information into the machine. The user interface is connected via an arm 30 to the cabinet 22. The user interface rotates about a tilt axis T and a vertical axis A so as to enable the user interface to be positioned at a location convenient for the patient.

Figure 2:
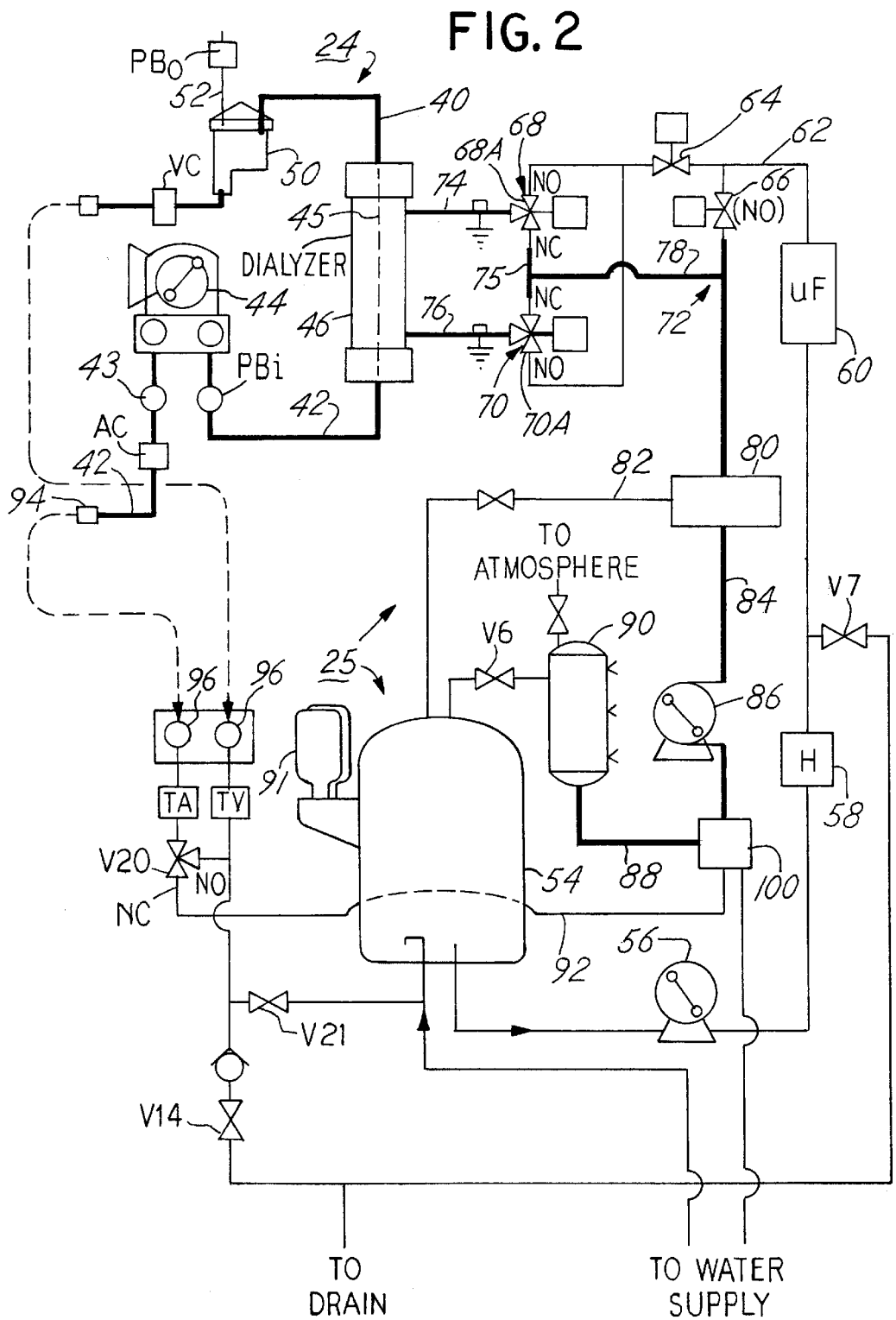
FIG. 2 is a schematic diagram of a representative extracorporeal blood circuit and dialysate circuit of the machine of FIG. 1, with the components thereof not related to the present invention omitted for the sake of conciseness and clarity.

FIG. 2 is a schematic illustration of the extracorporeal circuit 24 and dialysate preparation system 25 of the machine 10 of FIG. 1. In the embodiment of FIG. 2, blood is removed from the patient and introduced into the arterial line 42, and pumped by a blood pump 44 to the blood compartment or blood side of a dialyzer 46. An arterial pre-pump pressure sensor 43 is placed in the arterial line 42. Blood-borne toxins and excess water are removed from the blood through the membrane 45 of the dialyzer 46 into a dialysate circuit 72, and the blood is returned to the patient via the venous line 40. To prevent air from being introduced into the blood being returned to the patient, it is conventional in the dialysis art to place the air trap 50 in the venous line. The fluid level in the air trap 50 can be adjusted by known methods, and in FIG. 2 air is pumped into or out of the air trap 50 via line 52 to raise or lower the level in the air trap.

Further details of the particular extracorporeal circuit illustrated in FIG. 2 are not considered to be pertinent to the operation of the present invention, and can be found in the published PCT application of Kenley et al., publication no. WO 96/25214, or in the patent to Kenley et al. U.S. Pat. No. 5,591,344.

The dialysate preparation module 25 includes a fifty liter dialysate tank 54 storing a batch quantity of dialysate solution, and a pump 56 for pumping the solution from the tank through a heater assembly 58, a sterile ultrafilter 60, and into a line 62 leading to the dialysate side of the dialyzer 46. An inlet valve 64, bypass valve 66 and first and second inlet and outlet three way valves 68 and 70 are provided in the dialysate circuit 72. The dialysate circuit 72 includes an inlet line 74 and outlet line 76 from the dialyzer. The outlet line 76 is connected via valve 70 to a dialysate outlet line 78 that leads to a manifold 80. Valves downstream of the manifold 80 dictate whether the returning dialysate is directed to the tank 54 via line 82, or sent via line 84 to an ultrafiltration pump 86. The ultrafiltration pump 86 operates to remove precise volumes of dialysate solution from the dialysate circuit 72 into an ultrafiltration tank 90 via line 88. During the dialysis session, the fluid removed from the patient is pumped by the ultrafiltration pump from the dialysate circuit into the ultrafiltration tank 90, enabling precise measurement of the volume of fluid removed from the patient.

In the illustrated embodiment, dialysate solution is prepared in the tank 54 as a result of mixing chemicals from vessels 91 that are introduced into the tank 54 with reverse osmosis water from the water preparation module 23 of FIG. 1. The details are not considered pertinent and are described in the above-referenced Kenley et al. '344 patent. The particular details as to the dialysate preparation module, the manner in which the dialysate solution is prepared and circulated, are not considered to be a part of the invention and can be by any of several other known methods, such as using proportioning systems, such as described in the Grogan et al. patent, or otherwise.

During dialysis sessions, arterial pre-pump pressure is measured by the inlet pressure sensor 43 periodically (such as every 5 seconds) and the measurements recorded in a machine readable storage medium in the computer control system of the instrument. The measurements start when dialysis commences, after a predetermined number of seconds have elapsed (e.g., 20 seconds) to stabilize the blood flow and the pressure in the arterial line. Pressure measurements are also paused when the system slows or stops, such as in the case of an alarm, or when the pressure falls outside of preset high and low thresholds. In this manner, an average pressure over the course of a dialysis treatment can be calculated, such as by dividing the total sum of the pressure measurements by the number of measurements. This pressure is used during a calibration of the blood pump before the next treatment, and referred to as $P_c$ herein. Furthermore, the average pressure is also measured over a number of treatments (i.e., in an embodiment in which the blood tubing set and dialyzer are reused), and either regressed or averaged to get a more accurate figure for $P_c$. This data over the course of the treatment (and over multiple treatments) can be averaged or regressed to improve the ability to predict the pressure in the next treatment, and, significantly, can be used to accurately calibrate the flow rate of the blood pump.

After the treatment is over, the patient disconnects from the arterial and venous lines and places the arterial and venous line connectors into respective arterial and venous line connector ports 96 that are built in to the bulkhead of the instrument housing the extracorporeal circuit. These ports 96 are connected to tubing that allows cleaning and disinfection fluids to pass from the dialysate preparation or water treatment modules in the machine into the extracorporeal circuit for purposes of cleaning and disinfection, and from there to a drain. The ports, and the disinfection procedure, are described at length in the Kenley et al. '344 patent cited previously.

Figure 3:
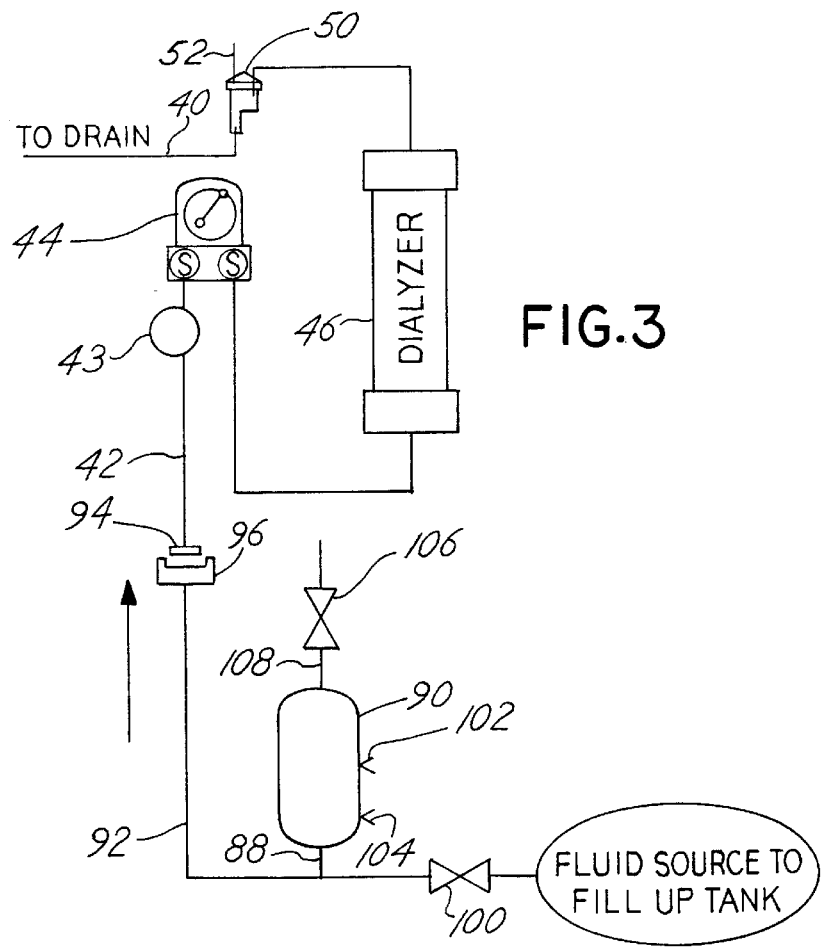
FIG. 3 is a schematic diagram showing the connection of the arterial line to the dialysate circuit and ultrafiltration tank of FIG. 2 after the treatment has ended, as would be the case when the blood pump calibration procedure is performed.

The fluid connection of the extracorporeal circuit to the rest of the machine, after dialysis is ended, is shown schematically in FIG. 3 to the extent relevant to the present discussion. The arterial line 42 terminates in a connector 94 that the patient inserts into a port 96 after the treatment is ended. The port 96 is connected to a line 98 in fluid communication with the ultrafiltration tank 90. The ultrafiltration tank is connected via a valve 100 to a source of water (or dialysate solution) that can be used in the calibration procedure described herein. The source could be water filtration apparatus in the machine, or the 50 liter tank in the machine, or some other convenient source. Fluid from the source is directed into the ultrafiltration tank 90 to fill the tank. The ultrafiltration tank has two level sensors 102 and 104 that define a precisely known volume of fluid (e.g., 100 ml). An atmospheric valve 106 is placed in a line 108 leading out of the top of the ultrafiltration tank 90. A sterile filter (not shown) is placed in the line 108.

After the treatment has ended, and prior to the next treatment, the blood pump is calibrated in accordance with the invention. A known volume of fluid is moved from the UF tank 90 at a predetermined RPM into the extracorporeal circuit and sent to drain. In the illustrated embodiment, the lines 92, 42 and 40 will be completely filled with fluid, such that the movement of fluid out of the ultrafiltration tank by the blood pump is exactly commensurate with the amount of fluid pumped through the extracorporeal circuit. The known volume of fluid is defined by the volume of fluid contained in the ultrafiltration tank between the levels indicated by the upper and lower level sensors 102 and 104, and will be precisely known. The time to move the volume of fluid is recorded automatically by a clock or timer in the computer system in the machine. The known volume of fluid moved during calibration divided by the time yields a flow rate. The flow rate divided by pump RPM gives a volume per revolution. The volume per revolution is the number that is used by the control software to precisely regulate the dose of dialysis during the next treatment. This calculation is performed by a conventional central processing unit in the control system, executing a software program having a calibration routine containing instructions as described herein.

During the above-described calibration procedure, the inlet pressure to the blood pump, measured at pressure sensor 43, is set to the calibration pressure $P_c$, obtained as described above. There are several ways of setting the calibration pressure $P_c$. One way is to place a variable flow restrictor in the line 92 and adjust the setting such that the inlet pressure recorded by pressure sensor 43 is to equal the value of $P_c$. Another way is to take advantage of the existing flow restrictions that are caused by the lines 42 and 92, the fixed head heights, and component pressure drops, and use the occluding atmospheric valve 106 at the top of the ultrafiltration tank. A presently preferred way of creating the calibration pressure at the inlet to the blood pump is as follows:

1. If the inlet pressure sensor 43 registers a pressure of 20 mm Hg more positive than the target calibration pressure $P_c$, then the atmospheric valve 106 is closed until the inlet pressure sensor 93 registers pressure of 20 mmHg more negative that the target calibration pressure, or until 10 seconds have elapsed.
2. After either of these conditions has been obtained, the atmospheric valve 106 is opened. The inlet pressure at 43 is then reevaluated, e.g., 10 seconds later.
3. Steps 1 and 2 are repeated throughout the calibration period.

This procedure effectively produces an oscillation in the inlet pressure about the calibration pressure. When graphed, the pressure oscillation takes the form of a saw-tooth wave. The pressure overshoots the target, then falls below the target, climbs again to overshoot the target, then falls below the target, etc. The mean pressure over time is the desired target calibration pressure $P_c$. The language used in the claims relating to the step of calibrating the blood pump while maintaining the inlet pressure at $P_c$ (or the mean inlet pressure) is intended to cover the situation in which the pressure is set at Pc directly and maintained there during the calibration period, or where the pressure is controllably varied about the pressure $P_c$, for example as just described.

In the situation when the value of $P_c$ is updated over multiple treatments or uses of the blood tubing set, the process proceeds as follows:

(1) the inlet pressure is recorded throughout the treatment as described above (i.e., pressure measurements are paused within 20 seconds of starting the blood pump or changing the blood pump speed, or whenever the pressure is outside of high or low limits);

(2) the pressure from successive treatments are averaged to derive a new value of Pc (sum the total pressure measurements and divide by the number of measurements, or alternatively sum the previous measurements of $P_c$, one per treatment, and divide by the number of previous treatments).

Figure 4:
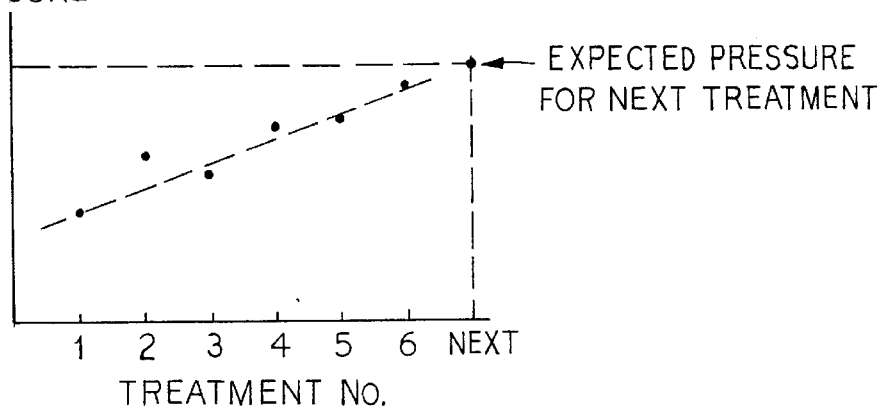
FIG. 4 is a graph of mean blood pump inlet pressure as a function of the number of treatments using the same blood tubing set, illustrating how pressure changes over a number of treatments can be used to derive an expected pressure for the next treatment.

(3) Alternatively, use a linear regression algorithm in which the pressure trend, treatment to treatment, predicts the pressure change for the next treatment, as shown in FIG. 4. One possible algorithm is as follows:

If treatment number (i.e., number of previous treatments)=1, set target calibration pressure $P_c$=measured average inlet pressure of treatment number 1; else if treatment number=2, set target calibration pressure=(measured average inlet pressure treatment #1+measured average inlet pressure treatment #2)/2 etc.

if treatment #>=5, set target calibration pressure=(sum of measured average inlet pressures from last 5 treatments)/5.

Note that the sensor used to measure the pressure during calibration is also the sensor used to measure the patient's arterial pre-pump pressure during dialysis, thus improving the accuracy of the calibration.

As a safety or redundancy check on the above procedure, in a preferred embodiment the calibration number calculated by this process is verified by comparing it to the previous calibration number for that blood tubing set (e.g., volume per stroke of blood pump) to see if the change (or calibration value) is outside a specified range. If the verification challenges the validity of the calibration, then calibration is repeated up to a predetermined number of times (say, 3). If, after repeated trials, the calibration is still outside of the specified range, then the calibration is deemed to have failed. The blood tubing set is replaced and/or the blood pump is serviced.

In another embodiment, in addition to using the smart point calibration to set the RPM of the blood pump during treatment, the inlet pressure measured during the treatment may be used to actively control the RPM of the blood pump in order to achieve a constant flow over varying pressure. For example, if the blood pump pumps a known volume of blood at a given RPM and particular inlet pressure and the pressure drops or rises, then the RPM of the blood pump may be adjusted to achieve a substantially constant flow of blood through the extracorporeal circuit. Calibration of the blood pump over a range of inlet pressures will assist in maintaining constant flow rates. The calibration over a range of inlet pressures may be done separately, or extrapolated from the known data of volume versus RPM at a given calibration pressure. In a representative embodiment, the substantially constant flow of blood can be maintained for at least one minute during the dialysis session, or preferably for longer periods of time, such as for 10 minutes or even longer.

Persons of skill in the art will appreciate that variations may be made to the preferred and alternative embodiments described above without departure from the true spirit and scope of the invention. This true spirit and scope is determined by the appended claims, to be interpreted in light of the foregoing.

I claim:

1. A method of operating a pump subject to repeated use, said pump placed in a fluid conduit, comprising the steps of:

(a) recording inlet pressures in said fluid conduit during a previous use of said pump;

(b) deriving, from said recordings of inlet pressure, a mean inlet pressure during said previous use of said pump;

(c) calibrating the flow rate of said pump, said step of calibrating performed while said inlet pressure to said fluid conduit is maintained at said mean inlet pressure; and (d) subsequently using said pump.

2. The method of claim 1, wherein said pump comprises a blood pump of a medical instrument.

3. The method of claim 2, wherein said blood pump is part of an extracorporeal blood circuit of a dialysis machine, and wherein said repeated uses of said pump comprise repeated uses of said pump in conjunction with dialysis sessions performed on a patient by said extracorporeal circuit and said dialysis machine.

4. The method of claim 1, wherein said step of calibrating comprises the steps of:

moving a known volume of fluid with said pump at a predetermined pump revolutions per minute;

measuring the time taken to move said known volume of fluid; and determining the volume of fluid moved by said pump per revolution;

wherein said step of moving is performed while said inlet pressure to said fluid conduit is maintained at said mean inlet pressure.

5. The method of claim 4, further comprising the steps of placing a restriction between a source of said known volume of fluid and the inlet to said fluid conduit, and adjusting said restriction so as to create an inlet pressure in said fluid conduit substantially matching said mean inlet pressure.

6. The method of claim 1, wherein:

said blood pump is incorporated into a medical instrument having a central processing unit, said step of recording comprises the step of reading measurements of inlet pressure to a computer-readable storage medium associated with said central processing unit, and said step of deriving is performed by said central processing unit retrieving said measurements from said storage medium and executing a software program to derive said mean inlet pressure from said measurements.

7. The method of claim 1, wherein during said step of calibrating the flow rate of said pump, said inlet pressure is varied periodically about said mean inlet pressure.

8. A method of calibrating a peristaltic blood pump of a hemodialysis machine, said hemodialysis machine having an extracorporeal circuit comprising an arterial line, a venous line, and a dialyzer, wherein said blood pump pumps blood from a patient through said arterial line and dialyzer and delivers said blood back to said patient via said venous line, comprising the step of:

recording inlet pressures in said arterial line during dialysis sessions for said patient;

deriving from said recorded inlet pressures a calibration inlet pressure $P_c$ to be used for calibration of said blood pump;

adjusting the inlet pressure of said arterial line and moving a known volume of fluid with said blood pump while maintaining said inlet pressure of said arterial line at said pressure $P_c$ to thereby calibrate said pump at said pressure $P_c$.

9. The method of claim 8, wherein said pressure $P_c$ is derived by regression of said recorded inlet pressures.

10. The method of claim 8, wherein said pressure $P_c$ is derived by averaging of said recorded inlet pressures.

11. The method of claim 8, wherein said step of moving comprises the step of moving a known volume of fluid by said blood pump with said blood pump operating at a predetermined rate of revolutions per minute.

12. The method of claim 11, wherein at least a portion of said known volume of fluid is stored in an ultrafiltration tank and drawn from said ultrafiltration tank through said extracorporeal circuit to a drain.

13. The method of claim 10, further comprising the steps of placing a restriction in a fluid line connecting said ultrafiltration tank to said arterial line, and adjusting said restriction during said step of moving so as to create an inlet pressure in said arterial line substantially matching said pressure $P_c$.

14. The method of claim 13, said dialysis machine comprises central processing unit and a computer-readable storage medium associated with said central processing unit, and wherein said step of measurements of inlet pressure are recorded on said computer-readable storage medium, and said derived volume per revolution is performed by said central processing unit by retrieving said measurements from said storage medium and executing a software program to calculate said volume per revolution.

15. The method of claim 8, further comprising the step of verifying the calibration of said pump to determine if said calibration is within a specified range.

16. A method of operating a dialysis machine having an extracorporeal circuit comprising a blood pump, an arterial line, a venous line and a dialyzer, comprising the steps of:

calibrating said blood pump at an inlet calibration pressure $P_c$ derived from recorded inlet pressures in said arterial line from an at least one previous dialysis session of said dialysis machine to thereby derive a relationship for said blood pump between said inlet calibration pressure $P_c$ and a known volume of fluid moved by said blood pump per revolution at said inlet calibration pressure $P_c$, and during a subsequent dialysis session of said dialysis machine, adjusting the speed of said blood pump to achieve a substantially constant flow of blood through said extracorporeal circuit regardless of changes in the inlet pressure of said arterial line during said use of said dialysis machine.

17. The method of claim 16, wherein said step of calibrating is performed by performing the following steps:

recording inlet pressures in said arterial line during previous dialysis sessions;

deriving from said recorded inlet pressures said calibration inlet pressure $P_c$;

adjusting the inlet pressure of said arterial line and moving a known volume of fluid with said blood pump while maintaining said inlet pressure of said arterial line at said pressure $P_c$ to thereby calibrate said pump at said pressure $P_c$.

18. The method of claim 16, wherein said step of adjusting is performed for at least one minute during the treatment of a patient during said subsequent dialysis session.

19. The method of claim 16, wherein said step of adjusting is performed for at least 10 minutes.

20. A method of operating a blood pump subject to repeated use, said blood pump placed in a fluid conduit comprising an extracorporeal circuit, comprising the steps of:

(a) recording inlet pressures in said fluid conduit during at least one previous use of said pump;

(b) deriving, from said recordings of inlet pressure, a mean inlet pressure during said at least one previous use of said pump;

(c) using a computed volume of fluid moved by said blood pump per revolution at said mean inlet pressure to calibrate said pump.

* * * * *